United States Patent [19]

Fattinger

[11] Patent Number: 5,479,260
[45] Date of Patent: Dec. 26, 1995

[54] OPTICAL PROCESS AND APPARATUS FOR ANALYSIS OF SUBSTANCES ON SENSOR SURFACES

[75] Inventor: Christof Fattinger, Blauen, Switzerland

[73] Assignee: Hoffmann-La Roche Inc., Nutley, N.J.

[21] Appl. No.: 429,214

[22] Filed: Apr. 24, 1995

Related U.S. Application Data

[63] Continuation of Ser. No. 217,340, Mar. 23, 1994, abandoned.

[30] Foreign Application Priority Data

Mar. 26, 1993 [CH] Switzerland ................. 927/93

[51] Int. Cl.[6] ............................. G01B 9/02
[52] U.S. Cl. ............... 356/361; 356/345; 385/12; 422/82.11; 436/805
[58] Field of Search ................. 356/345, 351, 356/354, 361, 128; 385/129, 12, 14; 422/82.05, 82.11; 436/805, 527

[56] References Cited

U.S. PATENT DOCUMENTS

| | | |
|---|---|---|
| 3,791,737 | 2/1974 | Johansson . |
| 3,982,810 | 9/1976 | Tamir et al. . |
| 4,047,795 | 9/1977 | Hughes et al. . |
| 4,082,425 | 4/1978 | Miller . |
| 4,102,560 | 7/1978 | Miller . |
| 4,426,130 | 1/1984 | Knop . |
| 4,647,544 | 3/1987 | Nicoli et al. . |
| 4,697,878 | 10/1987 | Kimura et al. . |
| 4,876,208 | 10/1989 | Gustafson et al. . |
| 4,877,747 | 10/1989 | Stewart . |
| 4,882,288 | 11/1989 | North et al. . |
| 4,931,384 | 6/1990 | Layton et al. . |
| 5,006,716 | 4/1991 | Hall . |
| 5,071,248 | 12/1991 | Tiefenthaler et al. ............ 356/128 |
| 5,082,629 | 1/1992 | Burgess, Jr. et al. . |
| 5,120,131 | 6/1992 | Lukosz ........................ 356/361 |
| 5,132,097 | 7/1992 | Van Deusen et al. . |

FOREIGN PATENT DOCUMENTS 63-276004  11/1988  Japan .

OTHER PUBLICATIONS

K. Tiefenthaler et al, Optics Letters, Apr. 1984, vol. 9, 137–139.
T. Tamir et al, J. of the Optical Society of America, Oct. 1971, vol. 61, 1397–1413.
M. Dakss et al, Applied Physics Letters, Jun. 1970, vol. 16, 523–525.
L. Johnson et al, Applied Physics Letters, Apr. 1981, vol. 38, 532–534.
R. McPhedran et al, J. Optics, Apr. 1982, vol. 13, 209–218.
W. Lukosz et al. Optics Letters, Oct. 1983, vol. 8, 537–539.
K. Tiefenthaler, et al, J. Opt. Soc. Am. B. Feb. 1989, vol. 6, 209–220.
S. Peng, J. Opt. Soc. Am. A, Aug. 1990, vol. 7, 1448–1456.

Primary Examiner—Samuel A. Turner
Attorney, Agent, or Firm—George M. Gould; William H. Epstein; Catherine A. Picut

[57] ABSTRACT

The optical process for analyzing substances is based on the measurement of the propagation properties of optical surface waves on sensor surfaces. In a wave guide layer structure in contact with a sample, guided light waves are decoupled with a grating coupler. The decoupling region of the grating coupler is imaged onto a position resolving detector so that the plane of the wave guide layer structure forms the object plane and the detection plane lies in the image plane of the optical imaging. The light distribution of the decoupled wave field in the image plane is measured with the detector and used to determine the analytical quantity to be measured. The device for carrying out the process consists of a suitable wave guide sensor with grating coupler, an imaging lens system and an optical detector (10).

52 Claims, 5 Drawing Sheets

1

OPTICAL PROCESS AND APPARATUS FOR ANALYSIS OF SUBSTANCES ON SENSOR SURFACES

This is a continuation of application Ser. No. 08/217,340, filed Mar. 23, 1994, now abandoned.

BACKGROUND OF THE INVENTION

The measurement of spectroscopic, physical quantifies in the immediate vicinity of a sensor surface with the aid of optical surface waves is known in the art. Recently, applications of this methodology have been gaining importance in the area of bioanalytical chemistry and biosensing. These new optical analytical processes are based on the interaction of the surface wave with the molecules to be detected. The detection of substances on the sensor surface is carried out, for example, by measuring changes in the refractive index and/or the optical absorption.

Optical surface waves are guided light waves which propagate in or on a wave guide layer structure along a surface. Optical surface waves may be guided for example, with an optical wave guide layer. The wave guide layer consists of a thin, dielectric optical layer on a planar substrate. Alternatively, the wave guide layer structure may consist of a thin metal layer on a substrate. In this case, the so called surface plasmon propagating on the metal layer represents the surface wave.

High, surface-specific detection sensitivity may be obtained by using very thin wave guide layers with a very high refractive index. The thickness of the wave guide layer in this case is clearly below the wave length of the guided light wave. The refractive index of the wave guide layer should be as high as possible, typically higher than 2.

It is known in the art that in order for coherent light to be coupled into or decoupled from the wave guide layer, using one or more optical diffraction gratings, so called grating couplers, is known in the art. Use of a bidiffractive grating coupler is advantageous. The bidiffractive grating coupler causes a directional separation between the decoupled light to be detected and the reflected or transmitted portions of the incident light beam. This makes possible background free detection of the light of the surface wave after decoupling.

By measuring the effective refractive index of the guided surface wave, changes in the refractive index in the immediate vicinity of the wave guide layer may be detected with high sensitivity. Prior art processes for investigating the binding between so-called receptor molecules and molecules which bind specifically to the receptor molecules immobilized on the wave guide surface are based on this detection scheme. In this way, molecular interactions (for example, binding reactions, sorption processes) may be analyzed.

The determination of the effective refractive index of the guided surface wave by measuring the coupling angle is state of the art. Determination of the effective refractive index of the guided surface wave by measuring the coupling angle, poses high demands on the planarity of the wave guide layer. Furthermore, these prior art processes for detecting molecules on sensor surfaces pose high demands on the stability of the angle measurement and on the accuracy of the position of the planar wave guide relative to the measuring device. These great demands must be considered as a disadvantage in regard to wide use of the measuring method.

A process for manufacturing wave guide layers with high refractive index on planar plastic substrates has been described in the German patent application P 42 28 853.3. This process offers the advantage that an optical grating for coupling or decoupling of light may be manufactured in a cost-efficient manner by embossing the plastic substrate.

SUMMARY OF THE INVENTION

The invention relates to a process for measuring the propagation properties of optical surface waves. The process is suited to the detection and characterization of molecules on sensor surfaces with the aid of optical surface waves. The invention also is directed to a device for carrying out the process and a sensor which comprises an optical wave guide layer with integrated optical diffraction grating as well as to the use of such sensors.

It is the objective of the invention to provide a high-sensitivity process and an apparatus for measuring the propagation properties of optical surface waves which is suited for the analysis of substances on sensor surfaces, permits an economically feasible manufacture of the sensor elements and insures simple handling of the sensor when used.

This objective is realized by an optical process and an apparatus which is characterized by the fact that the decoupling region of the grating coupler is imaged onto a position-resolving detector so that the plane of the wave guide layer structure forms the object plane and the detection plane lies in the image plane of the optical imaging and that the light distribution of the decoupled wave field resulting from the imaging is measured with the detector and used to determine the analytical quantity to be measured. The apparatus for carrying out the process comprises a sensor which possesses a surface to be brought into contact with the substance to be analyzed, an optical wave guide layer structure, a grating coupler in the layer structure for the decoupling of a guided light wave and a measuring device for measuring properties of the decoupled light wave, characterized by the fact that the measuring device contains an optical imaging system for imaging the decoupling region of the grating coupler and a position-resolving detector disposed in the image plane of the imaging system.

Imaging of the decoupled wave field may be carried out with a spherical or cylindrical lens. In place of the lens, a lens system, a Fresnel lens or a holographic lens may be used.

DETAILED DESCRIPTION OF THE INVENTION

Figure 1:
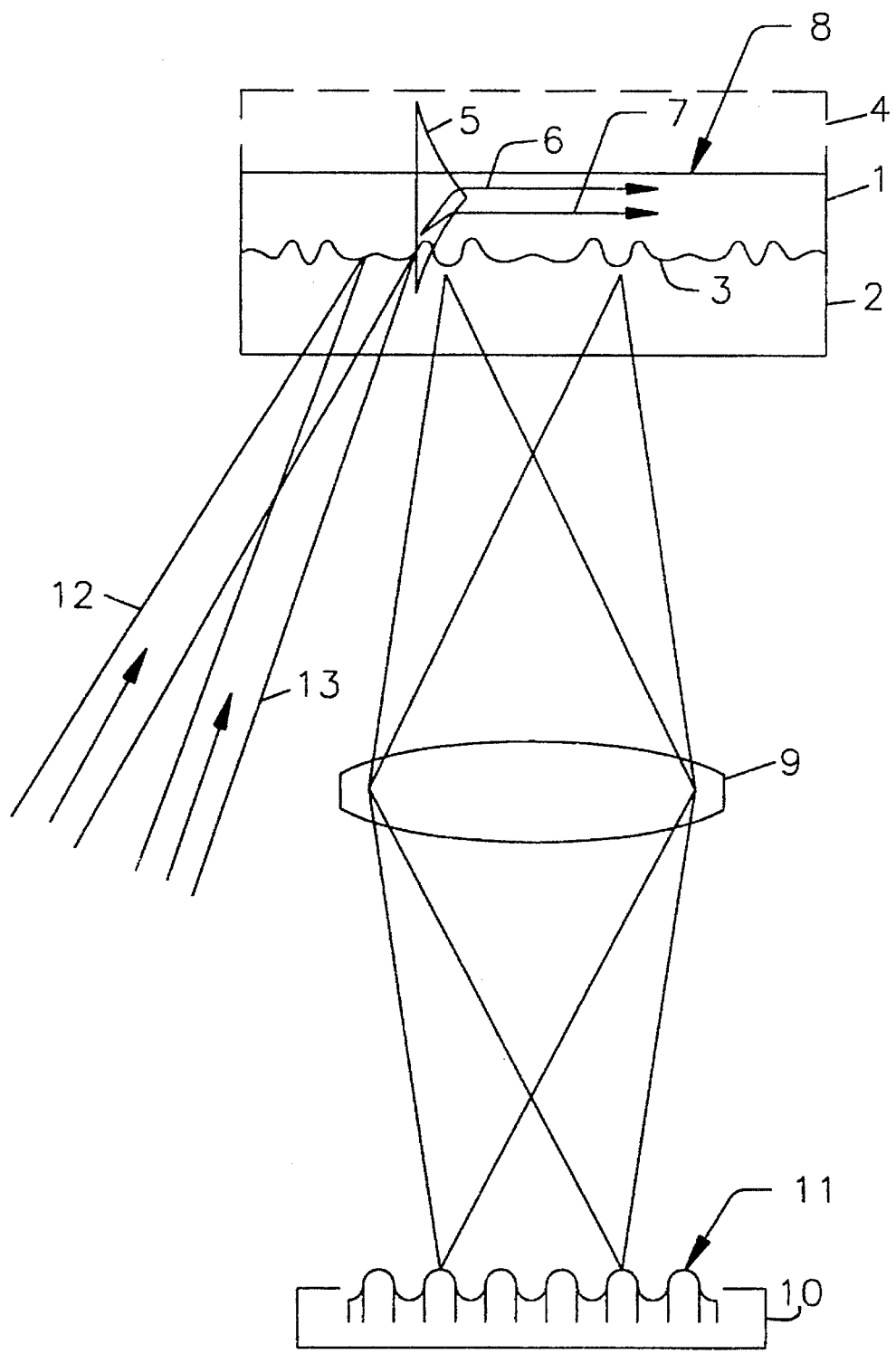

By imaging, different points on the wave guide layer are assigned to defined points in the detection plane. The grating coupler decouples the guided light waves continuously on their propagation path. Surprisingly, the propagation of the guided light waves in the plane of the wave guide layer may be sensed by imaging of the decoupled wave on a position-resolving detector. The light distribution of the decoupled wave field in the plane of the wave guide layer is characteristic for the propagation properties of the guided light waves. The light distribution in the detection plane is an image of the light distribution of the decoupled wave field in the plane of the wave guide layer and is used to determine the analytical quantity to be measured.

The inventive process with imaging of the decoupled wave field in the detection plane is suited to wave guide layer structures on substantially planar substrates. Imaging offers the advantage that the propagation properties of the guided light waves may be measured directly. The coupling angles of the decoupled light beams are not recorded by the imaging process. Small deviations of the wave guide layer structure from planarity play no role in the inventive measuring process. This characteristic of the measuring process simplifies the manufacture of the sensors significantly.

An additional advantage of the imaging is that small changes in position of the wave guide layer structure relative to the measuring system have no influence in tint approximation on the measured light distribution of the wave field in the detector plane. This characteristic of the measuring process simplifies the handling of the sensors during the measurement.

The inventive process permits several guided light waves to be imaged simultaneously in the detector plane. In this way, one of the guided light waves may be used as a reference wave. For example, the difference of the propagation properties between the measured wave and the reference wave is measured.

For the comparison of the propagation properties of the measured wave and the reference wave, the following measuring process has surprisingly been proven advantageous. In well-defined, band-like areas, the surface of the wave guide layer is prodded with a cover layer of a material of low refractive index. A light beam is coupled, for example, by a grating coupler into the planar wave guide so that the direction of propagation of the guided light runs parallel to the band-like areas of the wave guide provided with the cover layer. A portion of the guided light wave is shielded of from the sample on to the sensor surface by the cover layer. The portion of the guided light wave which propagates outside of the band-like areas of the wave guide with cover layer interacts with the molecules to be detected and serves as the measured wave. The portion of the guided light wave which propagates within the band-like areas of the wave guide with cover layer serves as reference wave. The propagation paths of the measured wave and reference wave run parallel to one another. By applying the cover layer, the wave guide layer structure is altered so that the effective refractive indices of the measured wave and reference wave differ slightly from one another.

The measured wave and reference wave are decoupled with a grating coupler and the decoupled wave field is imaged with a cylindrical lens system onto the detection plane. The cylinder axis of the imaging lens system in this case is perpendicular to the direction of propagation of the measured wave and reference wave. The two portions of the wave field which arise through decoupling of the measured and reference waves are superimposed by the one dimensional imaging of the cylindrical lens system producing a spatial periodic interference pattern in the detection plane. The periodicity of the interference pattern in the detection plane is given by the difference of the effective refractive indices of the measured wave and reference wave and by the imaging scale. By evaluating the spatial periodicity of the interference pattern, for example, by Fourier transformation of the measured light intensity distribution in the detection plane, the relative phase distribution of the measured wave and reference wave may be measured with very great precision. In this way, changes in the refractive index in the immediate vicinity of the wave guide layer may be sensed and assigned to the analytical quantity to be measured.

Applying a cover layer of $SiO_2$ on thin wave guides with high refractive index results in a difference between the effective refractive indices of the measured wave and reference wave which lie in a range which makes possible an evaluation of the interference pattern in the detection plane using a diode array. With a 1:1 imaging ratio between wave guide layer and detection plane, the period length of the interference pattern typically lies between ca. 20–100 micrometers.

A second analytical quantity is obtained by measuring the light intensity in the detection plane. The averaged intensity and/or fall-off of the intensity in the direction of propagation of the guided light wave gives information on attenuation (extinction) of the optical surface wave.

An alternative method for comparison of the propagation properties of two guided light waves is the following measuring process. Two light beams coherent to one another are coupled, for example, by a grating coupler into the planar wave guide whereby one of the light beams excites the transversal electric (TE) polarized mode of the wave guide and the other light beam excites the transversal magnetic (TM) polarized mode of the wave guide. The propagation paths of the two modes run parallel to one another or together on the same path. For thin wave guides with high refractive index, the interaction of the TE polarized mode and the TM polarized mode with the molecules to be detected on the wave guide surface is distinctively different. The effective refractive indices of the TE mode and the TM mode exhibit a considerable difference. The period length of the spatial beating of the two modes is typically smaller than 5 micrometers.

By using a bidiffractive grating coupler, the relative phase distribution of the TE mode and the TM mode may be measured in a technologically simple way. For this purpose, the wave guide layer in the area of the propagation paths of the two modes is provided with a bidiffractive grating coupler with suitably chosen period lengths for the two grating components. The TIE mode is decoupled via the grating component with the shorter period, the TM mode is decoupled via the grating component with the longer period. The decoupled wave field is imaged onto the detection plane. For this purpose, a spherical or cylindrical imaging lens system may be used. The two portions of the wave field resulting from decoupling of the TE mode and the TM mode are brought to interference with a polarizer whereby a spatial periodic interference pattern in the detection plane results. The periodicity of the interference pattern in the detection plane is given by the difference of the effective refractive indices of the TE mode and the TM mode, the difference of the period lengths of the two grating components of the bidiffractive grating coupler and by the imaging scale. By evaluating the spatial periodicity of the interference pattern, for example by Fourier transformation of the measured intensity distribution in the detection plane, the relative phase distribution of the TE mode and the TM mode may be measured with very high precision. In this way changes in the refractive index in the immediate vicinity of the wave guide layer may be sensed and assigned to the analytical quantity to be measured.

Optical diffraction gratings for coupling and decoupling of light from the planar wave guide may extend over limited regions of the wave guide layer as well as full-surface over the entire wave guide layer. The full-surface form of the coupler grating has the advantage that an expensive adjustment for coupling or decoupling of the light beams may be omitted.

In particular when using the inventive process in optical sensing and biosensing, use of a full-surface, bidiffractive grating coupler is advantageous. The bidiffractive grating coupler makes possible background-free detection of the light guided in the wave guide layer after decoupling, although the regions on the wave guide layer in which the coupling and decoupling of the guided light takes place partially overlap. The use of a full-surface, bidiffractive grating coupler offers the advantage of translation-invariant coupling and decoupling efficiency.

The full-surface, bidiffractive grating coupler may be used for coupling as well as for decoupling of the two modes. In this case, the TE mode is coupled via the grating component with the longer period and decoupled via the grating component with the shorter period. The TM mode is coupled via the grating component with the shorter period and decoupled via the grating component with the longer period.

Also when using the inventive process with a measured wave and a reference wave wherein the reference wave propagates in band-like areas of the wave guide with cover layer, coupling and decoupling is done preferably with a full-surface, bidiffractive grating coupler. Coupling of the measured wave and reference wave is done, for example, via the grating components with the longer period and decoupling of the measured wave and reference wave is done, for example, via the grating components with the shorter period. The period lengths of the two grating components of the bidiffractive grating coupler are chosen so that the decoupled wave field falls into the aperture of the imaging lens system and the angular range of the incident light beams come to lie aside from the imaging lens system.

The characteristic of translation invariance of the coupling and decoupling efficiency may also be obtained when using the inventive process with a measured wave and reference wave, in which the reference wave propagates in band-like areas of the wave guide which are provided with a cover layer. For this purpose, the cover layer is applied in the form of a raster of narrow parallel bands on the wave guide layer. The grating lines of the bidiffractive grating coupler are advantageously oriented at a right angle to the band-like areas of the wave guide which are provided with a cover layer. The directions of propagation of the measured wave and reference wave run parallel to the band-like areas with cover layer. Width and spacing of the band-like areas with cover layer are greater than the light wave length and smaller than the extension of the guided light wave perpendicular to the direction of propagation. The portion of the guided light wave which propagates between the band-like areas with cover layer serves as measured wave. The portion of the guided light wave which propagates within the band-like areas with cover layer serves as reference wave. The measured wave and reference wave are decoupled via the bidiffractive grating and the decoupled wave field is imaged with a cylindrical lens system onto the detection plane. The cylinder axis of the imaging lens system is perpendicular to the band-like areas with cover layer. The two portions of the wave field resulting from decoupling of the measured wave and reference wave are superimposed by the one-dimensional imaging of the cylindrical lens system producing an interference pattern in the detection plane. The spatial periodicity of the interference pattern in the detection plane may also be measured with great precision and assigned to the analytical quantity to be measured.

The angles of incidence of the light beams are to be chosen so that the coupling condition is satisfied. By a slight focusing of the incident beams, an expansion of the resonance curve for coupling is obtained so that an expensive adjustment for coupling of the light beams is avoided.

The selection of the angles of incidence for coupling is done, for example, with a suitable beam transmission system. An alternative method for selecting the angles of incidence consists of offering convergent beams and separating out narrow partial beams of the convergent beam with slit diaphragms. The position of the slit diaphragm in the convergent beam determines the angles of incidence for coupling of the guided light wave.

With a row of spatially addressable diaphragms, the selection of the angles of incidence may be done without the use of movable parts. The row of spatially addressable diaphragms for the incident light may, for example, consist of a liquid crystal cell with bar-shaped image elements disposed in a row. The addressed transparent image elements of the cell define the angles of incidence required for coupling.

In the field of bioanalytical chemistry and biosensing, refractometric measurements on sensor surfaces with the aid of optical surface waves are increasingly gaining in importance. With this method, molecular interactions may be investigated by measuring the variation of the refractive index in the immediate vicinity of the sensor surface. This sensor process may also be used to detect substances, for example, in gaseous and liquid samples.

A new method to detect substances, for example, in gaseous and liquid samples, is the measurement of the optical absorption in the immediate vicinity of the sensor surface. The absorption on the sensor surface is obtained by measuring the attenuation (extinction) of an optical surface wave. The absorption measurement in the case of a fixed wave length is carried out, for example, by measuring the light intensity in the detection plane with the angles of incidence adjusted to optimal coupling of the surface wave.

Figure 2:
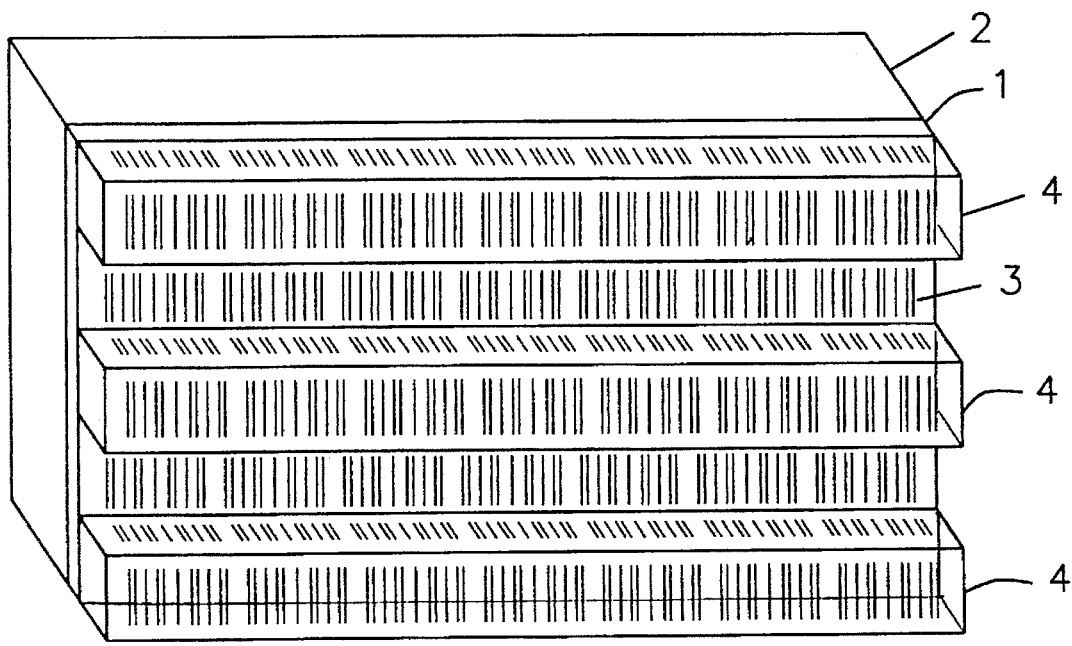
Figure 3:
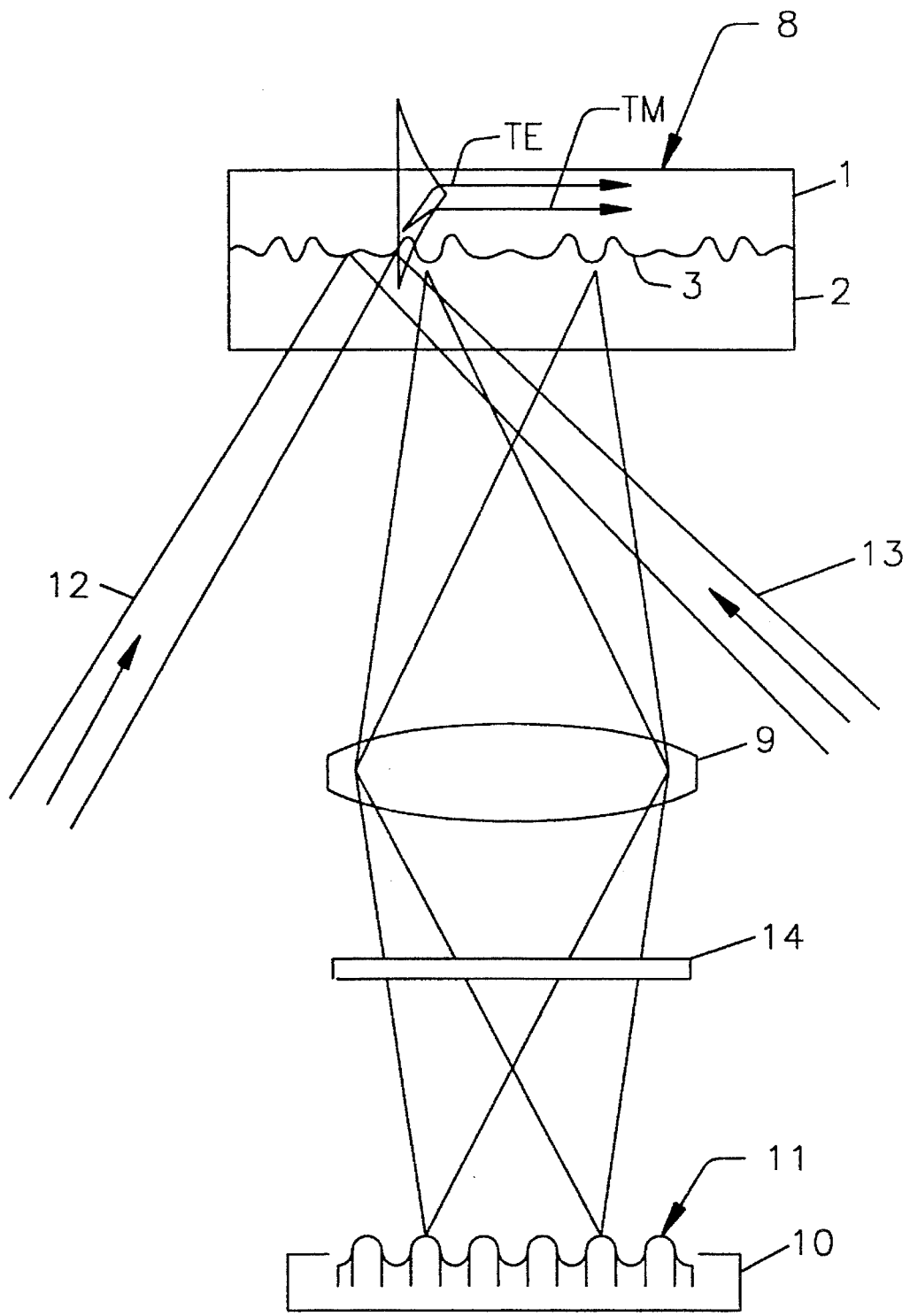
Figure 4:
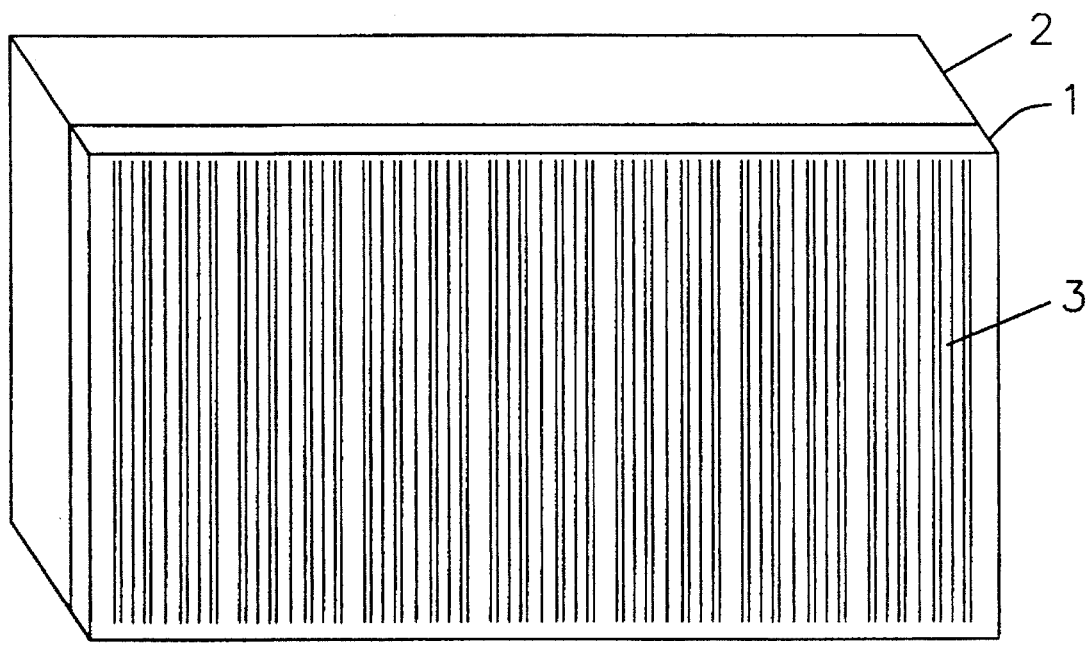
Figure 5:
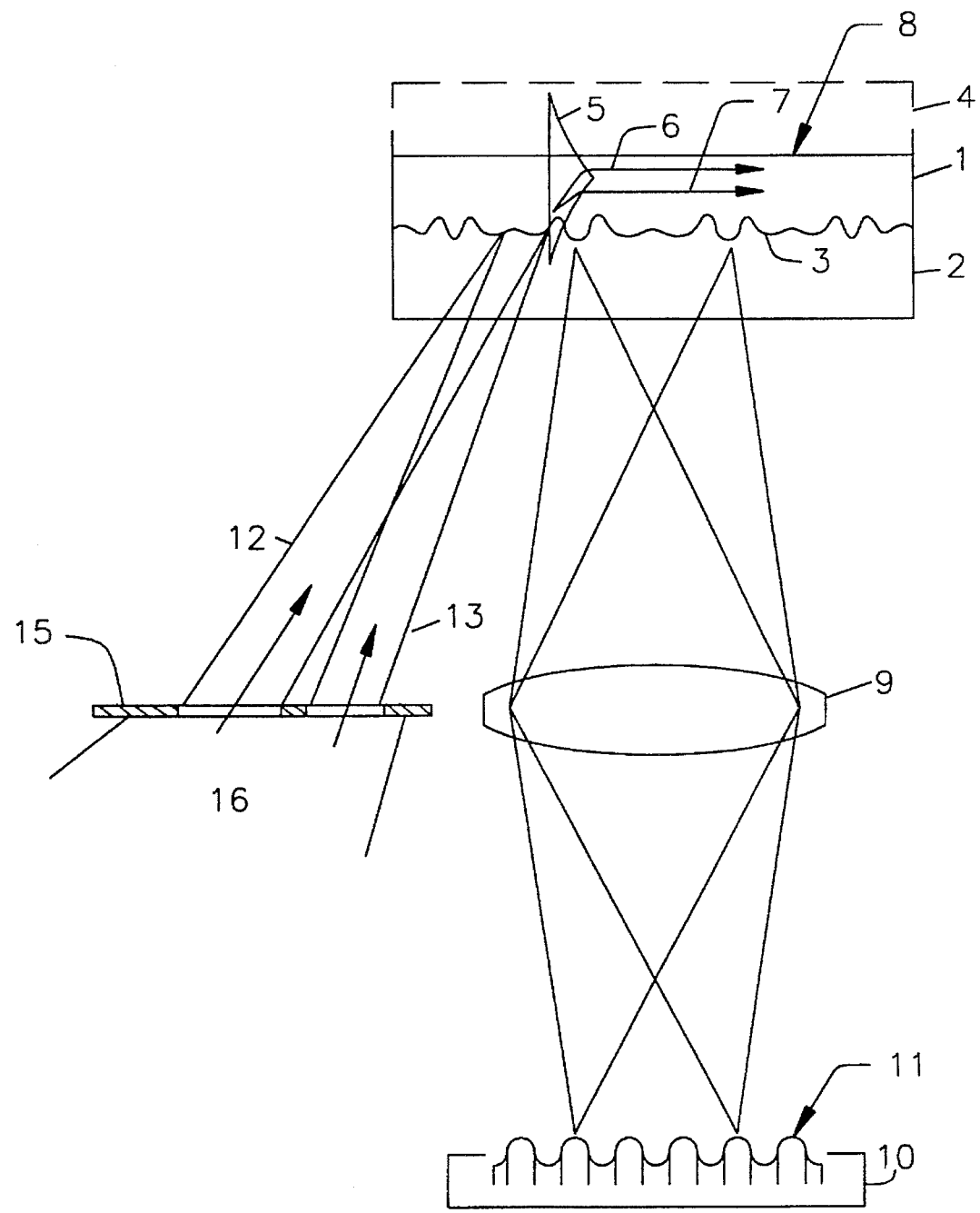

Exemplary embodiments of devices for carrying out the inventive process are described below with the aid of the accompanying drawings. Shown in highly schematic representation are:

FIG. 1 a section through a device for analyzing substances on sensor surfaces with the aid of optical surface waves, FIG. 2 a perspective representation of a sensor for analyzing substances with the device shown in FIG. 1, FIG. 3 a section through a device for measuring the position-dependent relative phase of the TE polarized mode and the TM polarized mode in a thin planar wave guide with high refractive index, FIG. 4 a perspective representation of a sensor for analyzing substances with the device shown in FIG. 3, FIG. 5 a schematic sectional representation of a device for measuring the propagation properties of optical surface waves with a row of spatially addressable diaphragms for the incident light.

In FIG. 1, a section through a device for analyzing substances on sensor surfaces is shown. A planar wave guide 1 on a planar substrate 2 is provided with a bidiffractive grating coupler 3. A portion of a guided light wave 5, the so-called reference wave 6, is shielded of from the sample onto the sensor surface by a cover layer 4. The other portion of the guided light wave 5, the so-called measured wave 7, interacts with the molecules to be detected on the wave guide surface 8. The measured wave and the reference wave are decoupled with the bidiffractive grating coupler. The decoupled wave field is imaged with a cylindrical lens 9 onto a position-resolving detector 10 resulting in a spatial periodic interference pattern 11 in the detection plane. By evaluating the spatial periodicity of the interference pattern, for example, by Fourier transformation of the intensity distribution measured in the detection plane, the position-dependent relative phase of the measured wave and reference wave may be measured with very high precision. In this way changes in the refractive index in the immediate vicinity of the wave guide layer may be sensed and assigned to the analytical quantity to be measured. The angles of incidence of light beams 12 and 13 must be chosen so that the coupling condition for the measured wave and the reference wave is satisfied. By slight focusing of the incident beams, an expansion of the resonance curve for coupling is obtained so that an expensive adjustment for coupling of the light beams is avoided.

FIG. 2 shows an embodiment of a sensor for analyzing substances with the aid of the device shown in FIG. 1. The sensor includes an optical wave guide layer 1 with a full-surface, bidiffractive grating coupler 3 on a planar substrate 2. The surface of the wave guide layer is provided with a cover layer 4 of a material with low refractive index in parallel, band-like areas. The direction of propagation of the guided light wave runs parallel to the band-like areas of the wave guide which are provided with a cover layer. The width of the band-like areas and their spacing are greater than the light wave length and smaller than the extension of the guided light wave perpendicular to the direction of propagation. The portion of the guided light wave which propagates between the band-like areas with cover layer, serves as measured wave. The portion of the guided light wave which propagates within the band-like areas with cover layer serves as reference wave.

FIG. 3 shows a device for measuring the position-dependent relative phase of the TE polarized mode and the TM polarized mode in a thin planar wave guide with high refractive index. A planar wave guide 1 on a planar substrate 2 is provided with a bidiffractive grating coupler 3. Two light beams 12 and 13 coherent to one another are coupled into the planar wave guide with the bidiffractive grating coupler whereby one of the light beams excites the transversal electric TE polarized mode of the wave guide and the other light beam excites the transversal magnetic TM polarized mode of the wave guide. The propagation paths of the two modes run parallel to one another or together on the same path. The interaction of the TE polarized mode and the TM polarized mode with the molecules to be detected on the wave guide surface is distinctively different. The two modes are decoupled with the bidiffractive grating coupler. The decoupled wave field is imaged with the lens 9 on a position-resolving detector 10 and brought to interference with a polarizer 14 resulting in a spatial periodic interference pattern 11 in the detection plane. By evaluating the spatial periodicity of the interference pattern for example, by Fourier transformation of the light intensity distribution measured in the detection plane, the position-dependent relative phase of the two modes may be measured with very high precision. In this way, changes in the refractive index in the immediate vicinity of the wave guide layer may be sensed and assigned to the analytical quantity to be measured.

FIG. 4 shows an embodiment of the sensor for analyzing substances with the aid of the device shown in FIG. 3. The sensor includes an optical wave guide layer 1 with a full-surface bidiffractive grating coupler 3 on a planar substrate 2.

FIG. 5 shows the sectional image of a further embodiment of a device for analyzing substances on sensor surfaces. The selection of the angles of the incident light is done with the aid of a row 15 of spatially addressable diaphragms in the ray path of a convergent beam 16. The addressed diaphragms of the row, switched to transparency, define the angles of incidence for coupling. Through the diaphragm openings, the slightly focused partial beams 12 and 13, suitable for coupling are separated out from the convergent beam 16.

I claim:

1. An optical process for analyzing a substance on a sensor surface, which comprises:

(a) generating guided light waves in a wave guide layer structure constituting the sensor surface, said guided light waves forming an object plane, (b) decoupling at least part of the guided light waves with a grating coupler to produce decoupled light waves, (c) imaging the decoupled light waves, to form a light distribution, said light distribution forming the detection plane.

(d) measuring the light distribution with a position-resolving detector, and (e) determining therefrom the analytical quantity of the substance.

2. A process according to claim 1, characterized by the fact that the wave guide layer structure includes an optical wave guide layer on a substrate.

3. A process according to claim 1, characterized by the fact that the wave guide layer structure includes a thin metal layer on a substrate.

4. A process according to claim 1, further comprising coupling guided light waves in the wave guide layer structure, wherein said coupling is done with the grating coupler.

5. A process according to claim 4, wherein coupling and decoupling of the guided light waves is done with a full-surface grating coupler.

6. A process according to claim 5, wherein said grating coupler is a bidiffractive grating coupler.

7. A process according to claim 1, characterized by the fact that decoupling of the guided light waves is done via different grating components of a bidiffractive grating coupler.

8. A process according to claim 1, wherein said imaging is done with a lens selected from the group consisting of a spherical lens, a lens system, a Fresnel lens and a holographic lens.

9. A process according to claim 1, wherein the position-resolving detector comprises a diode array.

10. A process according to claim 1, wherein at least one of the guided light waves propagates in an area of the wave guide layer structure with a cover layer.

11. A process according to claim 10, characterized by the fact that the cover layer consists of $SiO_2$.

12. A process according to claim 1, characterized by the fact that the guided light waves have different polarization.

13. A process according to claim 1, characterized by the fact that the guided light waves are coherent to one another.

14. A process according to claim 1, further comprising propagating guided light waves on paths in the wave guide layer structure, wherein said light waves have propagation properties, and wherein said paths are parallel to one another or are the same path.

15. A process according to claim 14, characterized by the fact that the difference of the propagation properties of the guided light waves is measured.

16. A process according to claim 1, further comprising polarizing the light distribution to create an interference pattern having a periodicity.

17. A process according to claim 16, characterized by the fact that a polarizer is located in the detection plane.

18. A process according to claim 16, characterized by the fact that the periodicity of the interference pattern is measured.

19. A process according to claim 16, characterized by the fact that the relative phase distribution of the guided light waves is measured.

20. A process according to claim 1, characterized by the fact that the imaging is done with a cylindrical lens, said lens being oriented at a right angle to the object plane.

21. A process according to claim 1, characterized by the fact that the light intensity of the light distribution in the detection plane is measured.

22. A process according to claim 4, wherein the incident light beams are slightly focused.

23. A process according to claim 4, further comprising directing incident light beams having angles of incidence into the wave guide layer structure, and selecting the angles of incidence using a beam transmission system.

24. A process according to claim 23, wherein the selecting is done using slit diaphragms disposed in the beam transmission system.

25. A process according to claim 24, characterized by the fact that the selecting is done using spatially addressable diaphragms disposed in the beam transmission system.

26. A process according to claim 25, characterized by the fact that the row of spatially addressable diaphragms consists of a liquid crystal cell with image elements disposed in a row.

27. Apparatus for analyzing substances on sensor surfaces comprising:
   (a) a sensor which possesses a surface to be brought into contact with the substance to be analyzed;
   (b) an optical wave guide layer structure;
   (c) a grating coupler in the layer structure for decoupling light waves guided in said layer structure;
   (d) an optical imaging system for imaging light waves decoupled by the grating coupler;
   (e) a position-resolving detector for detecting light waves resulting from the imaging and
   (f) a measuring device for measuring physical properties of the light waves.

28. Apparatus according to claim 27, characterized by the fact that the imaging system is a cylindrical lens system.

29. Apparatus according to claim 28, characterized by the fact that the cylindrical axis of the lens system is oriented at a right angle to the optical wave guide layer structure.

30. Apparatus according to claim 27, characterized by the fact that the imaging system is a Fresnel lens.

31. Apparatus according to claim 27, characterized by the fact that the imaging system is a holographic lens.

32. Apparatus according to claim 27, characterized by the fact that the detector is a diode array.

33. Apparatus according to claim 27, wherein said grating coupler is capable of coupling light waves guided in the layer structure.

34. Apparatus according to claim 33, wherein said grating coupler for coupling and decoupling light waves is a full-surface, bidiffractive grating coupler.

35. Apparatus according to claim 27, characterized by the fact that the sensor is provided in well-defined areas with a cover layer.

36. Apparatus according to claim 35, characterized by the fact that the cover layer consists of $SiO_2$.

37. Apparatus according to claim 35, characterized by the fact that the cover layer is applied in the form of parallel bands which run parallel to the light waves guided in the layer structure.

38. Apparatus according to claim 37, characterized by the fact that the width and spacing of the bands is each greater than the length of the longest light wave guided in the layer structure and smaller than the extension of any light waves which propagate perpendicular to the layer structure as a result of decoupling.

39. Apparatus according to claim 33, further comprising a beam transmission system for directing light waves to the wave guide layer structure.

40. Apparatus according to claim 39, characterized by the fact that the beam transmission system contains slit diaphragms.

41. Apparatus according to claim 40, characterized by the fact that the slit diaphragms are spatially addressable.

42. Apparatus according to claim 41, characterized by the fact that the spatially addressable slit diaphragms are liquid crystal cells.

43. A sensor for analyzing substances, comprising:
   (a) a sensor surface for contact with the substance to be analyzed,
   (b) an optical wave guide layer structure on the sensor surface,
   (c) a multi-diffractive grating coupler in the layer structure for decoupling a light wave guided in the layer structure, and
   (d) a cover layer applied to well-defined areas of the sensor surface.

44. An optical process for analyzing a substance on a sensor surface, which comprises:
   (a) generating guided light waves having a plane of propagation,
   (b) decoupling a portion of the guided light waves to produce decoupled light waves which propagate in a direction away from the plane of propagation of the guided light waves,
   (c) imaging the decoupled light waves,
   (d) measuring the physical properties of decoupled light waves, and
   (e) determining therefrom the quantity of the substance being analyzed.

45. The process of claim 44, wherein the decoupling is done by a multi-diffractive grating coupler.

46. The process of claim 45, wherein the decoupling is done by a bi-diffractive grating coupler.

47. The process of claim 44, further comprising polarizing the decoupled light waves to produce an interference pattern.

48. The process of claim 1, wherein said grating coupler is multi-diffractive.

49. The process of claim 1, wherein a part of the decoupled light waves propagate in a direction away from the object plane.

50. The process of claim 1, wherein a part of the decoupled light waves are free from guided light waves.

51. The apparatus of claim 27, wherein the grating coupler is a multi-diffractive grating coupler.

52. The sensor of claim 43, wherein the grating coupler is a full-surface bi-diffractive grating coupler.

* * * * *